United States Patent [19]

Abraham

[11] Patent Number: 5,554,377
[45] Date of Patent: Sep. 10, 1996

United States Patent

[54] NON-TOXIC ANIMAL REPELLENT

[76] Inventor: Carl J. Abraham, 3 Baker Hill Rd., Great Neck, N.Y. 11023

[21] Appl. No.: 362,250

[22] Filed: Dec. 22, 1994

[51] Int. Cl.$^6$ .................................................. A01N 63/00
[52] U.S. Cl. .................................... 424/405; 424/195.1
[58] Field of Search .................................. 424/403, 405, 424/195.1

[56] References Cited

PUBLICATIONS

Abstract (Basic): JP 1113308, May 2, 1989, "Nematode Repellent–Contains Extract of Asteraceae Tagetes Plant OBTD. Using Hydrophilic Organic Solvent or Comminuted Powder of Plant".

*Primary Examiner*—Thurman K. Page
*Assistant Examiner*—Sharon Howard
*Attorney, Agent, or Firm*—Levine & Mandelbaum

[57] ABSTRACT

A repellent incorporating the petals and/or oil of African Marigold (Tagetes Menuta) is applied to an area frequented by animals to deter them from entering or remaining in the area. The repellent can be obtained by drying the petals of the African Marigold and pulverizing them or extracting the oil by distillation and the use of organic solvents.

15 Claims, No Drawings

5,554,377

NON-TOXIC ANIMAL REPELLENT

BACKGROUND OF THE INVENTION

This invention relates to animal repellents, and more specifically, to a new composition of matter which can repel animals, and a method of making and using the composition.

Undomesticated animals, particularly deer, raccoons, rabbits and other rodents, remain a nuisance in suburban residential environments despite myriad efforts to keep them outside proximity to homes. The concept of repelling animals offers advantages over the use of toxins which not only result in the unnecessary death of animals, but also present a danger to people, and particularly children, and pets who may come in contact with such toxins.

Known repellents are of limited efficacy, especially those Which are not toxic to people and pets.

SUMMARY OF THE INVENTION

The aforementioned problems of the prior art are overcome by the instant invention which provides an animal repellent made from a natural growing plant which, although not harmful to people, has been demonstrated to repel animals such as deer, rabbits and other rodents, and even, to a degree, wild geese.

It is therefore an object of the invention to provide an animal repellent which is not harmful to people.

Another object of the invention is to provide an animal repellent involving a product which grows naturally.

Still another object of the invention is to provide an animal repellent which can be mixed with a carrier for use in an environment subject to animal infestation.

A further object of the invention is to provide a natural animal repellent which can be applied in either a liquid or dry form to accommodate various environments.

Still a further object of the invention is to provide an animal repellent which is derived from a flower species of a familiar genus.

DESCRIPTION OF THE PREFERRED EMBODIMENT

Although the literature suggests that marigold plants of the type found in the United States have some repellent qualities with respect to insects, they have been virtually ineffective in repelling animals. It has now been discovered that a species of the marigold genus no found on the North American continent but indigenous to Africa has an excellent repellent effect against animals as large as deer.

The species which provides the active ingredient for the repellent of the instant invention is Tagetes Menuta, referred to as African Marigold. The petals of the African Marigold may be used whole or they may be dried and crushed to form a powder. Alternatively, the oil of the African Marigold can be extracted, e.g., by steam distillation or the use of organic solvents, preferably hexanes.

African Marigold grown in Kenya has been found to be particularly effective as an animal repellent. However, African Marigold grown in other African countries yields excellent results as well.

The petals, in whole or crushed form, may be mixed with soil or fertilizer, or freely sprinkled over an area to be protected from animals. The oil extracted from the African Marigold can be sprayed onto trees, plants, walls of houses and other structures, garbages bags and pails, and other surfaces in the region to be protected. The oil can also be incorporated into polymeric materials to make, for example, garbage bags that would repel animals just as the powdered or dried petals of the African Marigold do.

Experiments were conducted to test the effectiveness of African Marigold as an animal repellent and its superiority over other species of Marigold grown in France, Italy, Mexico, and the United States.

EXAMPLE 1(a)

The first experiment was directed to the deterrence of raccoons from approaching food supplies in and around a residence. It was first observed that a raccoon traveled a particular path to a garbage pail placed outside of a residence each evening. The raccoon, seeking the supply of food contained therein, would knock over the garbage pail and tear open the bags inside leaving a mess of garbage strewn about the area. Dried petals of African Marigold were then sprinkled in the area around the path taken by the raccoon to the supply of food. For a period of approximately three weeks, thereafter, the raccoon refrained from taking the path that had been sprinkled and from contacting the garbage pail.

EXAMPLE 1(b)

The experiment of example 1(a) was repeated with a species of Marigold, known as *Calendula officinalis*. In separate trials, dried petals of *Calendula officinalis* grown in Mexico, France, Spain and The United States were sprinkled in the area around the path taken by the raccoon to the supply of food. In each trial, raccoons were not deterred and continued to knock over the garbage pail and tear open the bags inside containing discarded food and other garbage.

EXAMPLE 2(a).

Two dwarf rabbits were denied food on the evening prior to this experiment. On the morning of the experiment, a carrot was cut into pieces and placed in the rabbits' food dish. The carrot pieces were partially covered with sprinkles of the African Marigold. Neither one of the two rabbits would eat the carrot pieces which had been covered with sprinkles of African Marigold in the dish.

A second carrot which contained no sprinkles of African Marigold was then placed in the dish containing the pieces of the sprinkled carrot. The rabbits did not touch either of the two carrots then in the dish. A third carrot was cut into pieces which were placed outside of the dish. Both rabbits consumed the third carrot. Two more carrots were then placed outside of the dish and they, too, were consumed by the rabbits.

The sprinkled and unsprinkled carrots were left in the dish for the next six hours while a video camera recorded the scene surrounding the dish. Although the rabbits approached the two carrots, neither one ate the carrots or attempted to remove either of the carrots from the dish.

EXAMPLE 2(b)

The experiment of example 2(a) was repeated with the Marigold species known as *Calendula officinalis*. On separate occasions, carrots were sprinkled with samples of *Calendula officinalis* powder from Marigolds grown in Italy, Mexico, Spain and The United States. On each occasion, the rabbits consumed the carrots covered with the Calendula powder and were not repelled or deterred from eating them.

EXAMPLE 3(a)

A valuable tree on a golf course was regularly being used by a buck to clean his antlers thereby resulting in the stripping of the bark from the tree. An area surrounding the tree and having a radius of approximately two feet from the outer surface of the tree at ground level was sprinkled with petals of African Marigold. The tree was then observed for over one week during which the buck never approached the tree.

EXAMPLE 3(b)

The steps of example of 3(a) were repeated with the following exception. Instead of sprinkling the ground with petals of African Marigold, the tree itself was sprayed with oil extracted from African Marigold. The result was the same as in the experiment of example 3(a).

EXAMPLE 3(c)

The experiments of examples 3(a) and (b) were repeated with Marigold species known as *Calendula officinalis* grown in Italy, France, Mexico and The United States. In each case, the Marigold failed to repel deer.

EXAMPLE 4(a)

A grassy area where geese were known to congregate, within a park, was sprinkled with pulverized African Marigold. Thereafter, the geese stayed away from the sprinkled area. Food for the geese was then placed at the center of the treated grassy area. Geese then entered the area to consume the food but did not linger there. After consuming the food the geese went to other areas of the park which had not been treated with African Marigold.

EXAMPLE 4(b)

The experiment of example 4(a) was repeated with Marigold species known as *Calendula officinalis* grown in Italy, France, Spain and Mexico. Irrespective of which one of the latter four sources of Marigold was used, Geese entered the area sprinkled with *Calendula officinalis* with or without food present in the area.

From the foregoing is was observed that African Marigold (*Tagetes menuta*) is more effective than other forms of Marigold in repelling animals. In the case of some animals, e.g., geese, but not others, e.g., raccoons and rabbits, the hunger drive is strong enough to overcome the repellent powers of the African Marigold. However the African Marigold is sufficiently potent to repel animals with strong hunger drive when food is not at stake.

It is to be appreciated that the foregoing is a description of preferred embodiments of the invention to which variations and modifications may be made without departing from the spirit and scope of the invention. For example, the African Marigold petals or oil may be combined with other carriers or repellents, or used in materials from which camping facilities are fabricated, e.g., tents, sleeping bags, etc.

What is claimed is:

1. A method of repelling animals from an area comprising removing petals from African Marigold and spreading the petals of African Marigold about the area.

2. A method of repelling animals from an area according to claim 1 comprising drying the petals, then pulverizing the dried petals before spreading them without subjecting the pulverized petals to a solvent.

3. A method of repelling animals from an area according to claim 2 comprising pulverizing the petal into a powder before spreading them.

4. A method of repelling animals from an area comprising extracting the oil from the African Marigold by steam distillation and spreading said oil of African Marigold about the area.

5. A method of repelling animals from an area comprising obtaining oil of African Marigold by extracting the oil from the African Marigold by dissolving it in an organic solvent comprising a hexane.

6. A method of repelling animals from an area according to claim 1 comprising mixing the African Marigold with a carrier and placing the mixture of the carrier and African Marigold in the area.

7. A method of repelling animals from an area according to claim 6 wherein the carrier is soil.

8. A method of repelling animals from an area according to claim 6 wherein the carrier is fertilizer.

9. A method of repelling animals from an area according to claim 6 wherein the carrier is a polymeric material.

10. A method of repelling animals from an area according to claim 9 wherein the polymeric material is a constituent of a trash bag.

11. A method of repelling animals from an area according to claim 5 comprising mixing the African Marigold with a carrier and placing the mixture of the carrier and African Marigold in the area.

12. A method of repelling animals from an area according to claim 11 wherein the carrier is soil.

13. A method of repelling animals from an area according to claim 11 wherein the carrier is fertilizer.

14. A method of repelling animals from an area according to claim 11 wherein the carrier is a polymeric material.

15. A method of repelling animals from an area according to claim 14 wherein the polymeric material is a constituent of a trash bag.

* * * * *